(12) United States Patent
Inoue

(10) Patent No.: US 8,845,102 B2
(45) Date of Patent: Sep. 30, 2014

(54) OPHTHALMOLOGIC APPARATUS

(75) Inventor: Hiroyuki Inoue, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 187 days.

(21) Appl. No.: 13/398,053

(22) Filed: Feb. 16, 2012

(65) Prior Publication Data

US 2012/0218520 A1 Aug. 30, 2012

(30) Foreign Application Priority Data

Feb. 28, 2011 (JP) ................................. 2011-042656

(51) Int. Cl.
*A61B 3/00* (2006.01)

(52) U.S. Cl.
CPC .................................. *A61B 3/0075* (2013.01)
USPC .......................................... 351/245; 351/208

(58) Field of Classification Search
CPC ....... A61B 3/0075; A61B 3/0083; A61B 3/18
USPC .................................................. 351/245, 208
See application file for complete search history.

(56) References Cited

U.S. PATENT DOCUMENTS

| | | | | |
|---|---|---|---|---|
| 4,739,128 | A | * | 4/1988 | Grisham ........................ 200/6 A |
| 5,532,769 | A | * | 7/1996 | Miwa et al. .................... 351/205 |
| 5,764,341 | A | * | 6/1998 | Fujieda et al. ................ 351/221 |
| 6,733,129 | B2 | | 5/2004 | Masaki |
| 7,362,307 | B2 | * | 4/2008 | Wu et al. ........................ 345/161 |
| 7,662,092 | B2 | | 2/2010 | Miyagi et al. |
| 7,695,141 | B2 | | 4/2010 | Hara et al. |
| 2004/0267093 | A1 | | 12/2004 | Miyagi et al. |
| 2009/0079939 | A1 | * | 3/2009 | Mimura ......................... 351/245 |
| 2012/0218519 | A1 | | 8/2012 | Akiba |
| 2012/0218521 | A1 | | 8/2012 | Dobashi |

FOREIGN PATENT DOCUMENTS

| | | |
|---|---|---|
| CN | 100528071 C | 8/2009 |
| JP | 08-126608 A | 5/1996 |
| JP | 08-126611 A | 5/1996 |
| JP | 2002-108557 A | 4/2002 |
| JP | 3276682 B2 | 4/2002 |
| JP | 2002-369799 A | 12/2002 |
| JP | 2003-230535 A | 8/2003 |
| JP | 2004-275504 A | 10/2004 |
| JP | 3672447 B2 | 7/2005 |
| JP | 2006-130227 A | 5/2006 |
| JP | 2008-061715 A | 3/2008 |
| JP | 4250062 B2 | 4/2009 |

(Continued)

OTHER PUBLICATIONS

Jan. 30, 2014 Chinese Official Action in Chinese Patent Appln. No. 201210047788.2.

*Primary Examiner* — Jordan Schwartz

(74) *Attorney, Agent, or Firm* — Fitzpatrick, Cella, Harper & Scinto

(57) ABSTRACT

An ophthalmologic apparatus comprising: an inspection unit adapted to inspect an eye to be examined; an operation member; a first member including a recess portion and a projection portion provided on part of the recess portion; a second member which is integrally provided with the operation member and is configured to move in correspondence with tilting of the operation member while contacting the first member; and a driving unit adapted to move the inspection unit based on tilting of the operation member and to coarsely move the inspection unit in a case where the second member is in contact with the projection portion.

16 Claims, 12 Drawing Sheets

(56) References Cited

FOREIGN PATENT DOCUMENTS

| JP | 4265842 B2 | 5/2009 |
| JP | 4323209 B2 | 9/2009 |
| JP | 2009-268682 A | 11/2009 |

* cited by examiner

F I G. 11
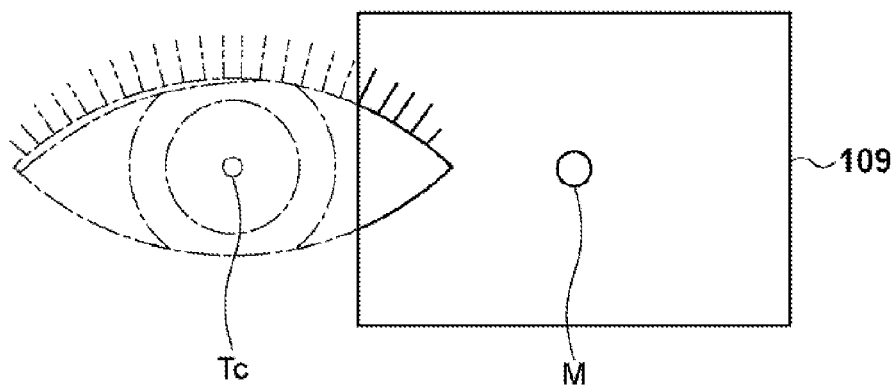
F I G. 12
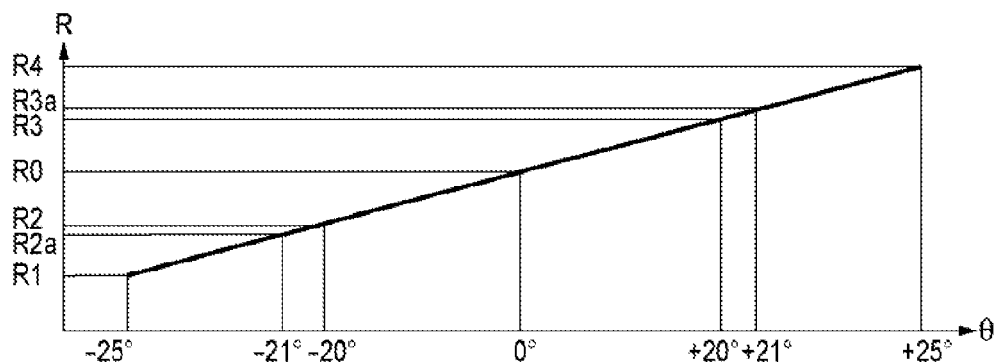
F I G. 13
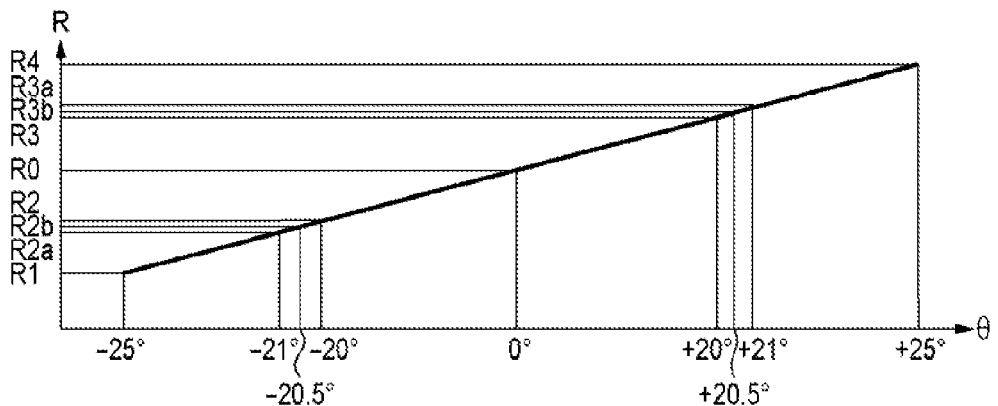

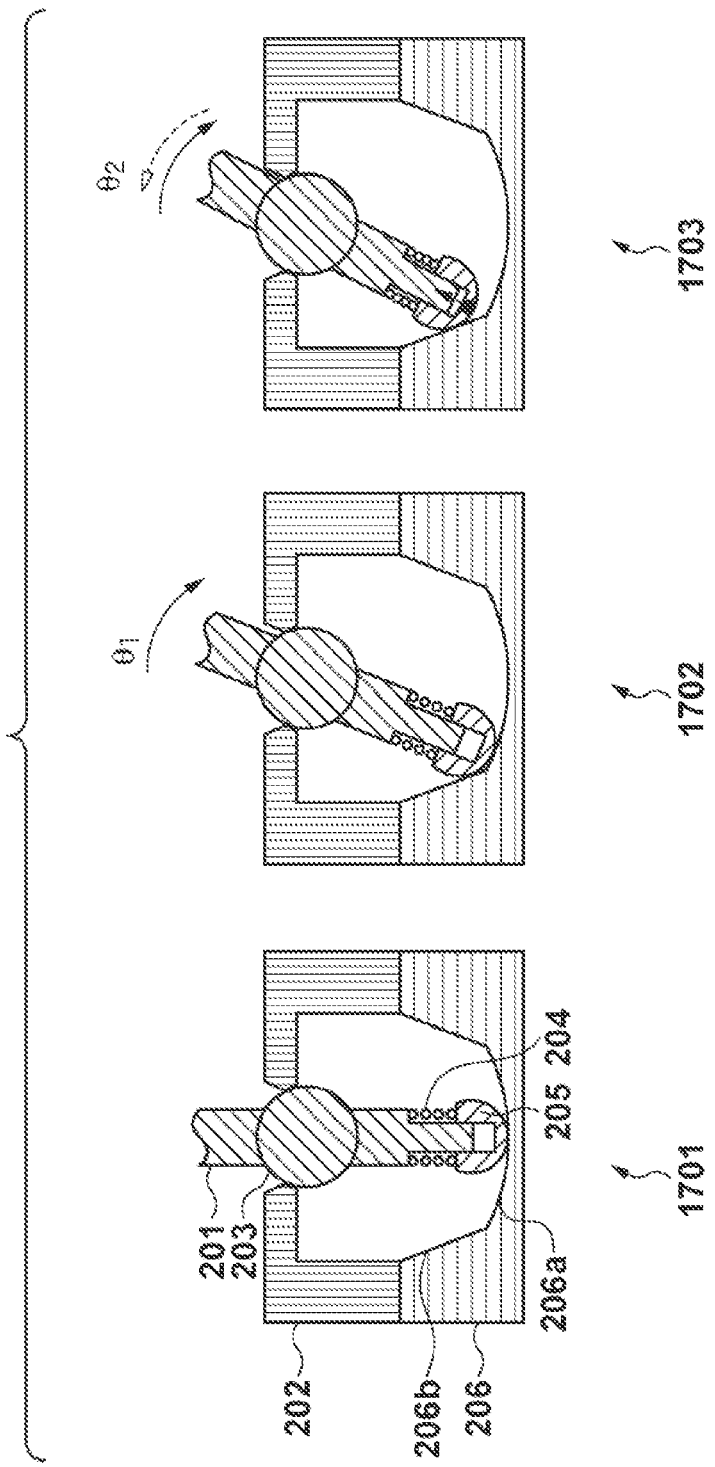

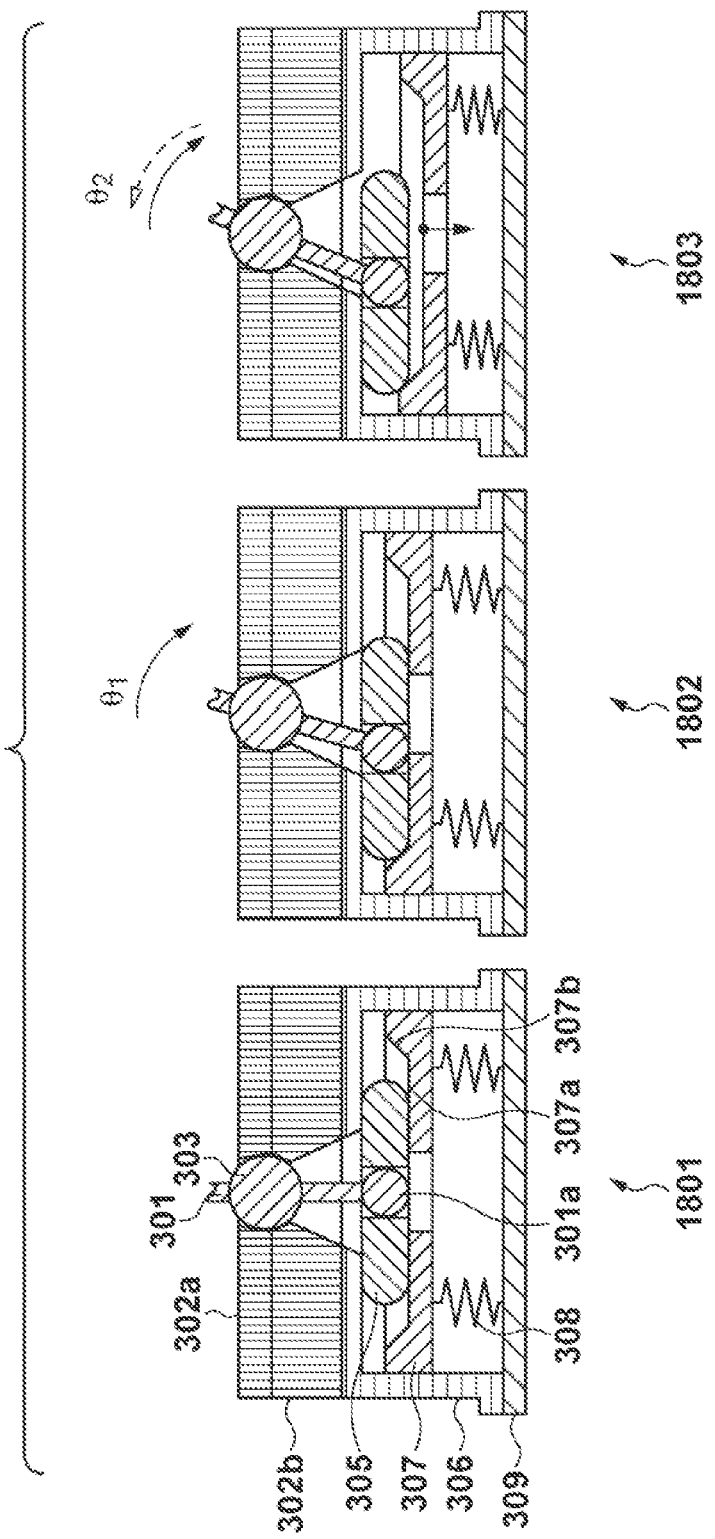

OPHTHALMOLOGIC APPARATUS

BACKGROUND OF THE INVENTION

1. Field of the Invention

The present invention relates to an ophthalmologic apparatus which aligns an optometric unit with an eye to be examined using a joystick mechanism to inspect, observe, and image the eye.

2. Description of the Related Art

Many ophthalmologic apparatuses include a base unit having a face rest which fixes the face of an object, an inspection unit which observes/images and measures the eye to be examined, a stage unit which moves the inspection unit back and forth, left and right, and up and down relative to the base unit, and a joystick mechanism which is operated to drive the stage unit.

Many conventional ophthalmologic apparatuses use a manual stage which mechanically links the joystick mechanism to the stage unit. The joystick mechanism mechanically drives the inspection unit. The joystick mechanism allows to perform fine operation of finely driving the inspection unit back and forth and left and right and coarse operation of coarsely driving the inspection unit back and forth and left and right. This makes it possible to finely align the inspection unit with the eye to be examined or largely move the inspection unit from one eye to the other eye.

Recently, however, an increasing number of ophthalmologic apparatuses include an electric stage owing to the advantages of auto alignment and the like. The electric stage is driven by a motor or the like, and hence cannot be moved by a mechanical link such as a conventional joystick mechanism. For this reason, according to Japanese Patent Laid-Open No. 8-126611, a trackball or the like is used as a driving instruction input device for the electric stage unit. However, such device greatly differs in operational feeling from the operation of a conventional manual stage, and hence often makes the examiner feel a sense of discomfort. In addition, the trackball is spaced apart from the roller, it is difficult to simultaneously operate them with one hand, thus posing a problem in terms of operability.

In order to solve the above problem, the ophthalmologic apparatus disclosed in Japanese Patent No. 4250062 includes a detection unit for detecting the tilt angle of a joystick mechanism in place of a trackball. There is also disclosed a transmission unit for outputting the signal detected by this detection unit to a drive motor and transmitting the output of the drive motor to the inspection unit. In this case, this ophthalmologic apparatus uniformly controls the moving velocity of the optometric unit in accordance with the tilt angle of the joystick mechanism. However, since this apparatus uniformly controls the moving velocity of the optometric unit in accordance with the tilt angle of the joystick mechanism, it is impossible to perform fine operation and coarse operation which can be done by a mechanical joystick mechanism. This therefore also poses a problem in terms of operability.

In order to implement fine operation and coarse operation like those of a mechanical joystick mechanism in an ophthalmologic apparatus including an electric stage, the apparatus requires a joystick mechanism capable of performing both the operation of holding a tilt angle for fine operation and the operation of restoring a tilt angle to a neutral angle for coarse operation. This makes it possible to perform position control of the electric stage unit in fine operation, thereby allowing to perform fine alignment. In addition, it is possible to perform velocity control in coarse operation. This can quickly perform the operation of largely moving the inspection unit.

Japanese Patent Laid-Open Nos. 2006-130227 and 2008-61715 disclose ophthalmologic apparatuses each including a joystick mechanism having operation members respectively provided for fine operation and coarse operation. Operational feeling similar to that of the joystick mechanism using the manual stage is implemented by using the joystick mechanism which is provided with the operation member for maintaining a tilt angle for fine operation with frictional force and is also separately provided with the operation member for restoring to the neutral position for coarse operation.

Japanese Patent Nos. 3276682 and 4323209 disclose a joystick mechanism which switches between using frictional force for holding a tilt angle and not using frictional force. This implements a joystick mechanism which can perform both the operation of holding a tilt angle and the operation of restoring to the neutral angle.

Japanese Patent Laid-Open Nos. 2002-369799 and 2009-268682 disclose techniques of implementing fine operation and coarse operation by using the same operation member. These techniques use the joystick mechanism in a fine operation region where when the joystick mechanism is tilted within a predetermined tilt angle, frictional force is used to hold the tilt angle of the joystick mechanism, and position control is performed on the electric stage. On the other hand, the joystick member is used in a coarse operation region where when joystick mechanism is tilted to an angle larger than a predetermined tilt angle, the mechanism restores to a predetermined angle, and coarse operation control is performed on the electric stage. This implements a joystick mechanism for an electric stage which exhibits good operability with a simple arrangement.

The joystick mechanisms disclosed in Japanese Patent Laid-Open Nos. 2006-130227 and 2008-61715, however, require two operation members for fine operation and coarse operation, and hence its arrangement is complicated. In addition, the joystick mechanisms disclosed in Japanese Patent Nos. 3276682 and 4323209 require the mechanism of switching between using frictional force and not using friction force, and hence its arrangement is complicated.

The joystick mechanisms disclosed in Japanese Patent Laid-Open Nos. 2002-369799 and 2009-268682 implement fine operation and coarse operation with a simple arrangement. However, these joystick mechanisms implement tilting in an arbitrary direction throughout 360° with two rotatable shafts perpendicular to each other and has friction mechanisms provided for the respective shafts to hold the tilt in the fine operation region. For this reason, according to these mechanisms, when the operator tries to tilt the joystick mechanism toward the intermediate position of each shaft, frictional force acts from the two shafts, resulting in uneven operational feeling. With such uneven operational feeling, it is difficult for the examiner to operate the joystick mechanism in a desired aligning direction. This may lead to a deterioration in alignment accuracy or a decrease in throughput.

The joystick mechanism disclosed in Japanese Patent No. 4323209 generates frictional force on a spherical moving member which moves synchronously with the tilting of the joystick mechanism, and hence can obtain operational feeling independently of the tilting direction. However, the arrangement of this mechanism is complicated, as described above.

In consideration of the above problems, the present invention provides an ophthalmologic apparatus including a joystick mechanism which can obtain uniform operational feeling with a simple arrangement.

SUMMARY OF THE INVENTION

According to one aspect of the present invention, there is provided an ophthalmologic apparatus comprising: an inspection unit adapted to inspect an eye to be examined; an operation member; a first member including a recess portion and a projection portion provided on part of the recess portion; a second member which is integrally provided with the operation member and is configured to move in correspondence with tilting of the operation member while contacting the first member; and a driving unit adapted to move the inspection unit based on tilting of the operation member and to coarsely move the inspection unit in a case where the second member is in contact with the projection portion.

According to another aspect of the present invention, there is provided an ophthalmologic apparatus comprising: an inspection unit adapted to inspect an eye to be examined; an operation member; a first member including a recess portion and a projection portion provided on part of the recess portion; and a second member which is integrally provided with the operation member and is configured to move in correspondence with tilting of the operation member while contacting the first member; wherein in a case where the second member is in contact with the projection portion, a distance between a tilt center of the operation member and the second member is shorter than a distance between the tilt center of the operation member and the second member in a case where the second member is not in contact with the projection portion.

Further features of the present invention will be apparent from the following description of exemplary embodiments with reference to the attached drawings.

BRIEF DESCRIPTION OF THE DRAWINGS

FIG. 11 is a view for explaining a state in which the center of the eye to be examined is spaced apart from the alignment mark on the monitor;

FIG. 12 is a schematic view showing the relationship between tilt angles and outputs from the detection unit with a dead band;

FIG. 13 is a schematic view showing the relationship between tilt angles and outputs from the detection unit with hysteresis;

FIG. 17 is a sectional view of an operation unit according to the second embodiment; and FIG. 18 is a sectional view of an operation unit according to the third embodiment.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

(First Embodiment)

Figure 1:
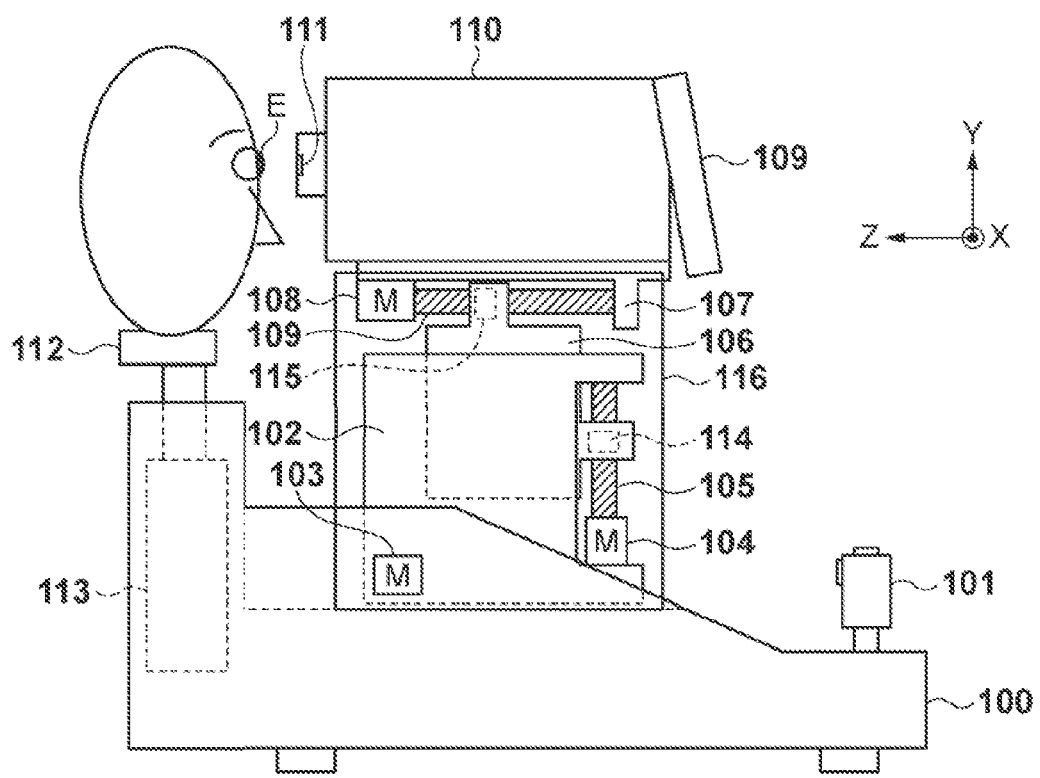
FIG. 1 is a view showing a schematic arrangement of an ophthalmologic apparatus according to the first embodiment.

The first embodiment of the present invention will be described with reference to the accompanying drawings. FIG. 1 is a view showing the schematic arrangement of an ophthalmologic apparatus according to the first embodiment. The ophthalmologic apparatus includes a base unit 100 having a face rest portion 112 which supports the face of an object, a driving unit 116 and operation unit 101 provided on the base unit 100, and an inspection unit 110 mounted on the driving unit 116. The inspection unit 110 includes an optical system which performs inspection (including measurement, observation, and imaging) on the eye to be examined. An LCD monitor 109 as a display member for the observation of an eye E to be examined is provided on the examiner side end portion of the inspection unit 110.

A driving mechanism 113 allows the face rest portion 112 to move in the upward/downward direction (Y-axis direction). The examiner performs tilting operation of the operation unit 101 to issue driving instructions for the driving direction, driving amount, and driving velocity of the driving unit 116 so as to align the position of the inspection unit 110, that is, the position of a lens 111, with the eye E, thereby performing inspection, observation, imaging, and the like. The driving unit 116 includes driving mechanisms corresponding to the respective axes to move the inspection unit 110 in the X, Y, and Z directions set in advance.

(X-Axis)

A frame 102 can move in the leftward/rightward direction (X-axis direction) relative to the base unit 100. A driving mechanism in the X-axis direction includes an X-axis driving motor 103 fixed on the base unit 100, a feed screw (not shown) coupled to the output shaft of a motor, and a nut (not shown) which can move on the feed screw in the X-axis direction and is fixed to the frame 102. As the X-axis driving motor 103 rotates, the frame 102 moves in the X-axis direction through the feed screw and the nut.

(Y-Axis)

A frame 106 can move in the upward/downward direction (Y-axis direction) relative to the frame 102. A driving mechanism in the Y-axis direction includes a Y-axis driving motor 104 fixed on the frame 102, a feed screw 105 coupled to the output shaft of a motor, and a nut 114 which can move on the feed screw 105 in the Y-axis direction and is fixed to the frame 106. As the Y-axis driving motor 104 rotates, the frame 106 moves in the Y-axis direction through the feed screw 105 and the nut 114.

(Z-Axis)

A frame 107 can move in the forward/backward direction (Z-axis direction) relative to the frame 106. A driving mechanism in the Z-axis direction includes a Z-axis driving motor 108 fixed on the frame 107, a feed screw 109 coupled to the output shaft of a motor, and a nut 115 which can move on the feed screw 109 in the Z-axis direction and is fixed to the frame

106. As the Z-axis driving motor 108 rotates, the frame 107 moves in the Z-axis direction through the feed screw 109 and the nut 115.

Figure 2:
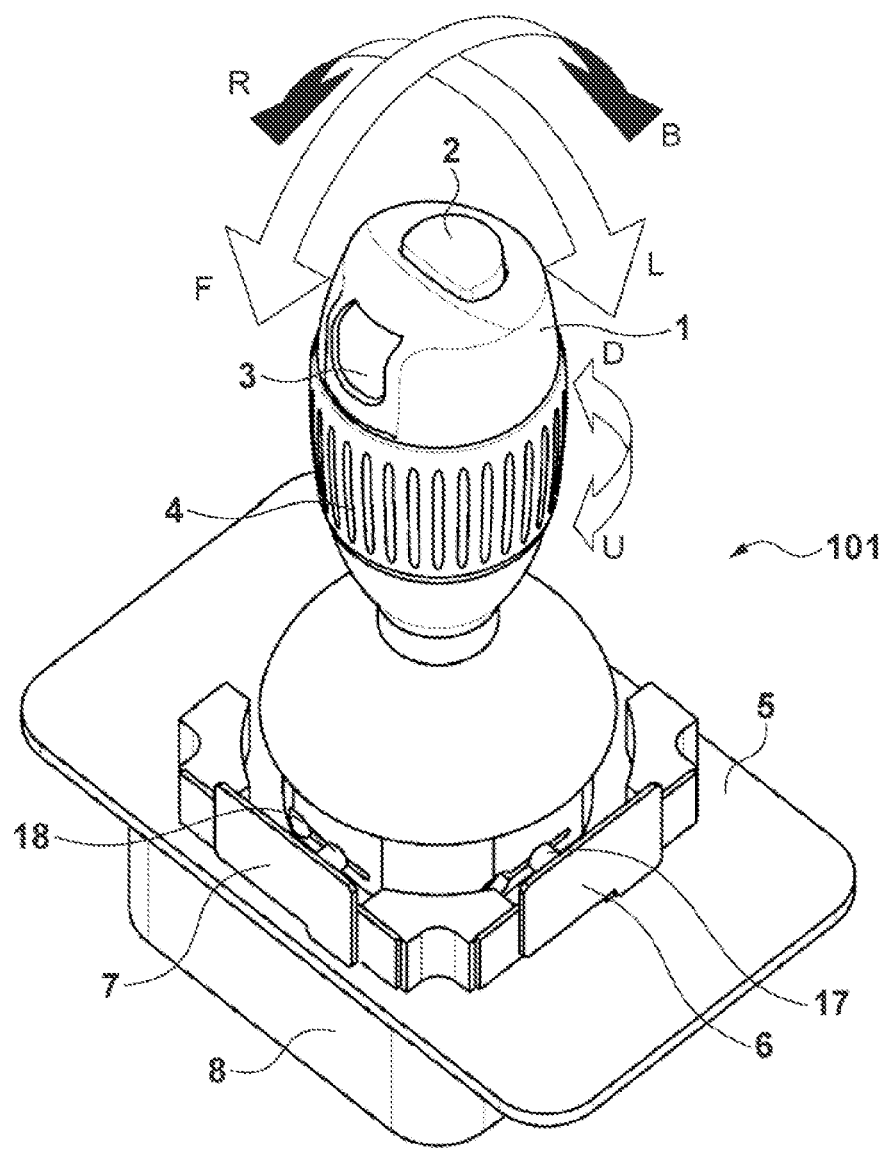
FIG. 2 is a perspective view of an operation unit.

FIG. 2 is a perspective view of the operation unit 101. The operation unit 101 is configured to move the inspection unit 110 in three-dimensional directions by issuing driving instructions for the driving direction, driving amount, and driving velocity of the driving unit 116 (to drive the driving unit 116 to move the inspection unit 110 based on the tilt of an operation member 1). The operation unit 101 includes a joystick 1 (an example of the operation member), a measurement button 2, an operation invalidating unit 3, a rotating dial 4, a bearing base 5, a first detection unit 6, a second detection unit 7, an operating force generation unit 8 (an example of the first member including a recess portion 14a and a projection portion 8b provided on part of the recess portion 14a) for generating operating force such as frictional force, holding force, or the like (to be described later), a first slide pin 17, and a second slide pin 18.

When the examiner tilts the joystick 1 for performing various kinds of operations in the direction indicated by a double-headed arrow LR, the inspection unit 110 moves in the eye-width direction of the eye to be examined. When the examiner tilts the joystick 1 in the direction indicated by a double-headed arrow FB, the inspection unit 110 moves in a direction to approach or separate from the eye to be examined. The inspection unit 110 moves in the upward/downward direction when the examiner rotates the rotating dial 4. The measurement button 2 is placed on the top of the joystick 1. The measurement button 2 is used as a start button for inspection, observation, imaging, and auto alignment. This allows the examiner to perform operations from alignment to measurement using only the operation unit 101. Other constituent elements will be described later.

Figure 3:
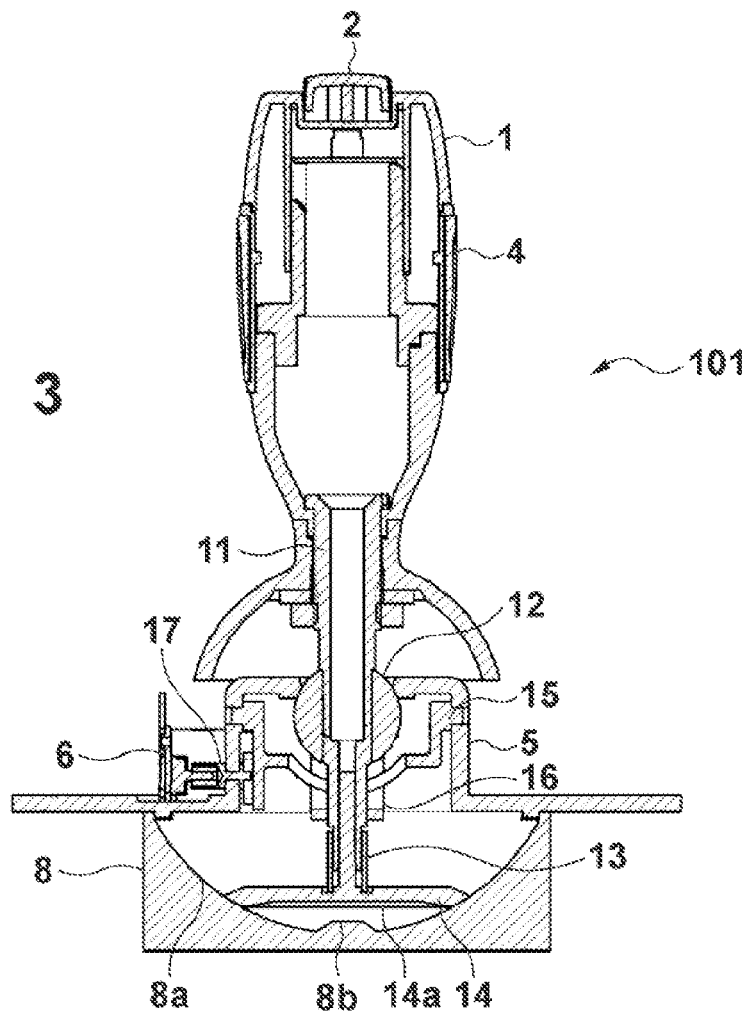
FIG. 3 is a sectional view of the operation unit according to the first embodiment.

FIG. 3 is a sectional view obtained by cutting the operation unit 101 shown in FIG. 2 in the direction of the double-headed arrow LR. The operation unit 101 further includes a joystick shaft 11, a central ball 12, a compression spring 13 (an example of an elastic member provided between the tilt center and a second member 14 in the joystick 1), a moving portion (an example of the second member which is integrally provided with the operation member and can move in correspondence with the tilting of the operation member 1 in contact with the first member 8), a first motion direction conversion unit 15, and a second motion direction conversion unit 16.

The joystick shaft 11 is jointed inside the joystick 1. The bearing base 5 is placed below the operation unit 101. The central ball 12 is attached to the joystick shaft 11 on the lower side of the opening portion of the bearing base 5. The central ball 12 has a spherical shape, and is biased toward the opening portion of the bearing base 5 by the compression spring 13 (to be described later). This allows to perform tilting operation using, as the tilt center, the curvature center of the central ball 12 as a central member serving as a supporting point when the joystick 1 tilts.

An arrangement for detecting a tilt angle from the non-tilt position of the operation unit 101 will be described below. The first motion direction conversion unit 15 and the second motion direction conversion unit 16, each having a recess shape, are arranged perpendicular to each other below the central ball 12 attached to the joystick shaft 11. The first motion direction conversion unit 15 and the second motion direction conversion unit 16 convert the tilting motion of the joystick 1 into linear motion.

Central rotation shafts are formed on the two ends of the first motion direction conversion unit 15 and second motion direction conversion unit 16 so as to be fitted in the central rotation holes formed in the bearing base 5. The first motion direction conversion unit 15 and the second motion direction conversion unit 16 are supported so as to be rotatable about the central rotation holes of the bearing base 5. In this case, the central rotation holes are preferably flush with the curvature center of the central ball 12. In addition, the recess portions of the first motion direction conversion unit 15 and second motion direction conversion unit 16 are provided with holes through which the joystick shaft 11 extends, and are fitted on the joystick shaft 11. Other constituent elements will be described later.

Figure 4:
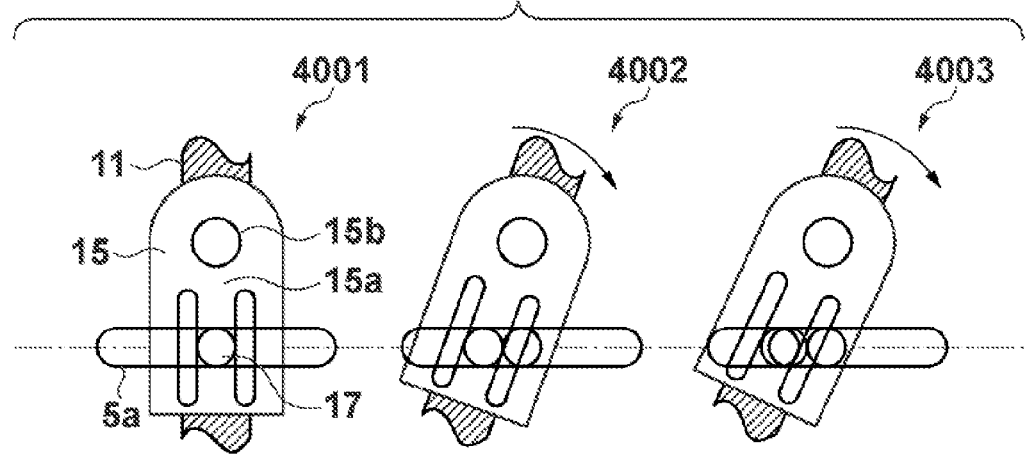
FIG. 4 is a schematic view showing detecting operation by a first detection unit.

The operation of the first motion direction conversion unit 15 when the joystick 1 is tilted in the direction indicated by the double-headed arrow FB will be described below with reference to FIG. 4. As indicated by reference numeral 4001, a groove portion 15a is formed in one end portion of the first motion direction conversion unit 15 in the same direction as that of the axis of the joystick shaft 11, and is placed so as to allow the first slide pin 17 to fit therein. In addition, the first slide pin 17 is fitted in a groove portion 5a formed in the bearing base 5 and can freely move only in the horizontal direction in FIG. 4. The first slide pin 17 is joined to the input shaft (not shown) of the first detection unit 6. In this case, the first detection unit 6 is a direct-acting position detection unit, which is a direct-acting potentiometer. When the joystick 1 is tilted, the joined joystick shaft 11 also tilts, as indicated by reference numerals 4002 and 4003. Along with this operation, the first motion direction conversion unit 15 fitted on the joystick shaft 11 rotates about central rotation shafts 15b on the two ends. When the first motion direction conversion unit 15 rotates, the first slide pin 17 fitted in the groove portion 15a moves along the groove portion 5a of the bearing base 5, thereby moving the input shaft of the first detection unit 6.

With the above operation, the resistance of the first detection unit 6, the resistance of the direct-acting potentiometer in this case, changes, thereby allowing to detect the tilt angle of the joystick 1.

Note that the operation to be performed when detecting the tilt angle of the joystick 1 in the direction indicated by the double-headed arrow LR is the same as the operation of detecting a tilt angle in the direction indicated by the double-headed arrow FB by using the second motion direction conversion unit 16, the second slide pin 18, and the second detection unit 7. A detailed description of the operation will therefore be omitted. As described above, using the first detection unit 6 and the second detection unit 7 can uniquely detect the tilt angle of the joystick 1 in an arbitrary tilting direction.

Although this embodiment uses the direct-acting position detection unit as a detection unit, it is possible to use a detection unit which detects a rotational angle. In this case, for example, there is available a method of joining the input shaft of a rotary potentiometer to one end of the central rotation shaft of each of the first motion direction conversion unit 15 and second motion direction conversion unit 16. The detection unit which detects a rotational angle can also use a method of detecting a tilt angle by using a sensor such as an encoder instead of a rotary potentiometer.

An arrangement for generating operating force will be described next. Referring to FIG. 3, the moving portion 14 is placed below the joystick shaft 11. A hollow portion is formed on the lower end side of the joystick shaft 11. The center shaft of the moving portion 14 is fitted in the joystick shaft 11. The moving portion 14 is slidable in the direction of the joystick shaft 11 with respect to the joystick shaft 11. A disk shape in which the recess portion 14a having a recess shape in the central portion is formed below the center shaft of the moving portion 14. The operating force generation unit 8 joined to the bearing base 5 is provided below the moving portion 14. An approximate spherical surface 8a centered on the curvature center of the central ball 12 is formed on the operating force generation unit 8. A restoration member having the projection portion 8b having a projection shape is formed on the central portion of the approximate spherical surface 8a. The compression spring 13 as an elastic member is provided between the joystick shaft 11 and the moving portion 14. The compression spring 13 is compressed to generate a biasing force. This biasing force biases the central ball 12 against the bearing base 5, and also biases the moving portion 14 against the operating force generation unit 8.

Figure 5:
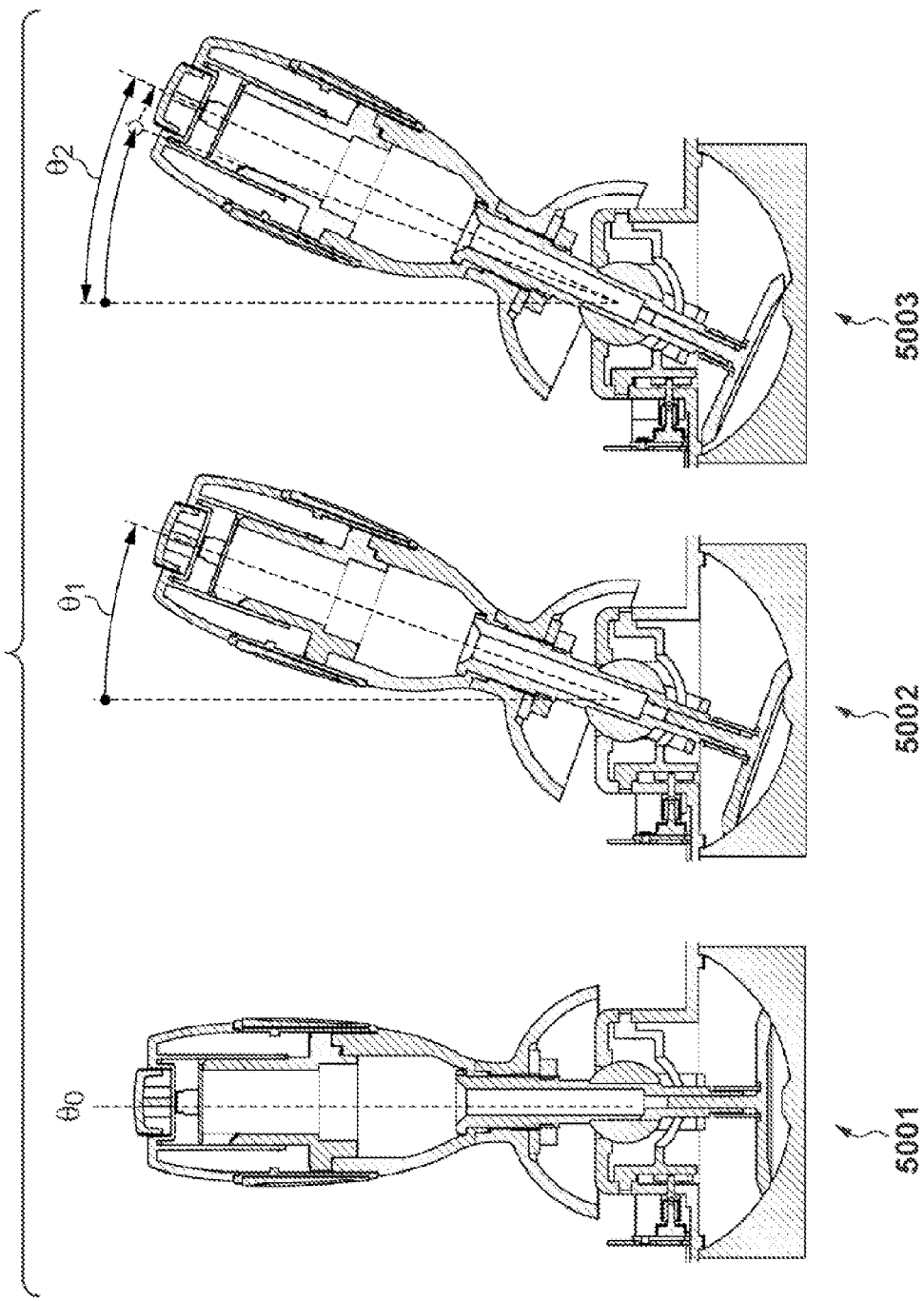
FIG. 5 is a sectional view of the operation unit when a joystick tilts.

The operation of the operation unit 101 when the joystick 1 is tilted will be described with reference to FIG. 5. FIG. 5 is a sectional view obtained by cutting the operation unit 101 shown in FIG. 2 in the direction of the double-headed arrow RL.

Reference numeral 5001 denotes the neutral state of the joystick 1; 5002, the state in which the joystick 1 tilts by a predetermined angle $\theta_1$; and 5003, the state in which the joystick 1 tilts by a predetermined angle $\theta_2$. In this case, the predetermined angle $\theta_1$ is the maximum tilt angle of a tilt holding region, and the predetermined angle $\theta_2$ is the maximum tilt angle of the tilt restoration region.

A case will be described first in which the joystick 1 is tilted in the tilt holding region (between the tilt angles $\theta_0$ to $\theta_1$) (which will also be referred to as the first case or a state before the second member 14 comes into contact with the projection portion 8b). In the tilt holding region, the compression spring 13 biases the moving portion 14 against the approximate spherical surface 8a of the operating force generation unit 8. At this time, frictional force is generated between the moving portion 14 and the operating force generation unit 8. This frictional force allows to hold the tilt angle of the joystick 1 (the compression spring 13 acts to hold the position of the second member 14 relative to the first member 8). In addition, since the approximate spherical surface 8a of the operating force generation unit 8 is formed with a curvature centered on the tilt center, the compression spring 13 does not stretch and contract even if the moving portion 14 is moved in an arbitrary direction within the tilt holding region. This can generate constant frictional force regardless of the operating direction of the joystick 1. This makes it possible to hold the operating force constant in an arbitrary direction. In this case, as will be described later, the driving unit 116 drives the inspection unit 110 to finely move (for example, move the inspection unit 110 to a position corresponding to a tilt angle).

A case will be described in which the joystick 1 is tilted to the tilt restoration region (which will be described as the second case or a case in which the moving portion 14 is in contact with the projection portion 8b). When the examiner tilts the joystick 1 to the tilt restoration region, the inclined surface formed on the outer circumference of the recess portion 14a of the moving portion 14 comes into contact with the restoration portion (projection portion) 8b of the operating force generation unit 8 (see reference numeral 5002). When the examiner further tilts the joystick 1, the moving portion 14 moves in the axial direction by the axial component of the joystick shaft 11 upon reception of a force acting from the inclined surface of the moving portion 14 (obliquely right upward indicated by reference numeral 5002) (see reference numeral 5003; the distance between the tilt center of the joystick 1 and the second member 14 is smaller than that before the second member 14 comes into contact with the projection portion 8b). At this time, the compression spring 13 is compressed. Since an operating force corresponding to the degree of compression of the compression spring 13 is required, the examiner can recognize that he/she has operated the joystick 1 to the tilt restoration region. This allows the user to easily recognize that the fine operation and coarse operation of the inspection unit 110 have been switched. In this case, when the examiner stops holding the joystick 1, the stretching force of the compression spring 13 generates a force to restore the moving portion 14 toward the center. With this restoring force, the joystick shaft 11 and the joystick 1 restore to the predetermined angle $\theta_1$ indicated by reference numeral 5002. At this time, as will be described later, the driving unit 116 drives the inspection unit 110 to perform coarse operation (for example, the driving unit 116 moves the inspection unit 110 at a constant velocity regardless of the tilt angle).

Figure 6:
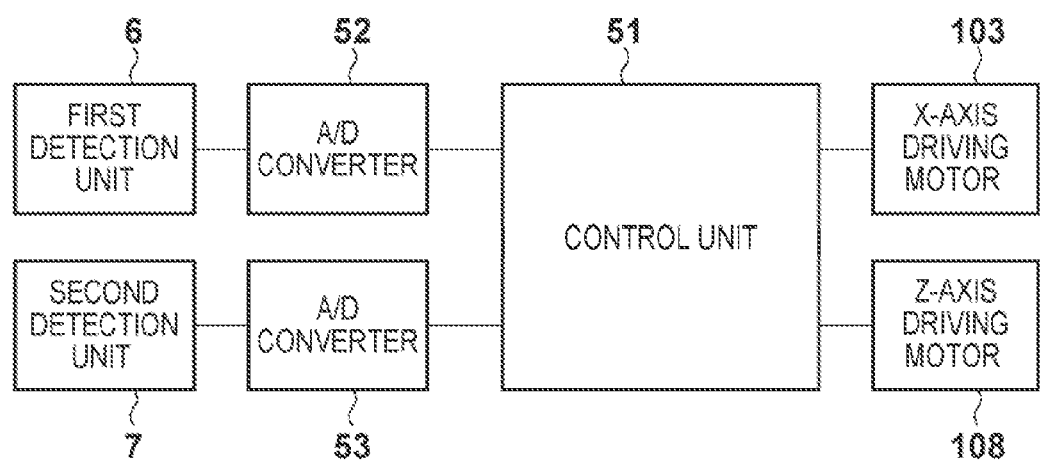
FIG. 6 is a functional block diagram according to the first embodiment.
Figure 7:
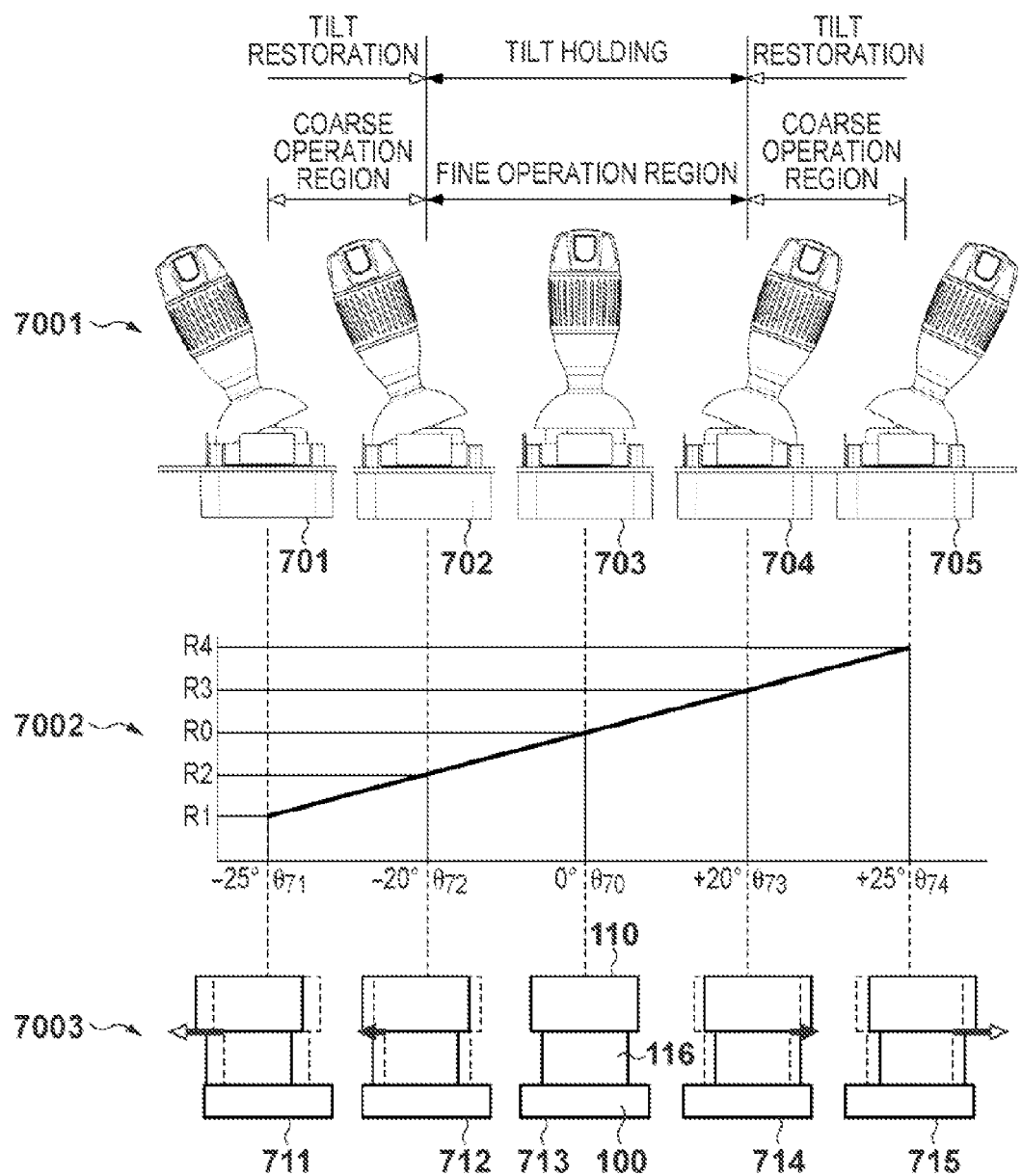
FIG. 7 is a schematic view showing the tilting positions of a joystick, outputs from a detection unit, and the movement of an inspection unit.

FIG. 6 is a functional block diagram for explaining control according to this embodiment. The first detection unit 6 is connected to a control unit 51 via an A/D converter 52. Likewise, the second detection unit 7 is connected to the control unit 51 via an A/D converter 53. The control unit 51 is connected to the X-axis driving motor 103 and the Z-axis driving motor 108. The control unit 51 controls the X-axis driving motor 103 and the Z-axis driving motor 108 by transmitting driving signals to them based on signals input from the first detection unit 6 and the second detection unit 7 via the A/D converters 52 and 53.

Reference numeral 7001 denotes a view showing postures 701 to 705 of the operation unit 101 each corresponding to the tilt angle $\theta$ of the joystick 1 in the direction indicated by the double-headed arrow LR; 7002, a graph showing the relationship between the postures 701 to 705 of the operation unit 101 and resistances R as outputs from the second detection unit 7; and 7003, a view showing operation states 711 to 715 of the inspection unit 110 corresponding to the postures 701 to 705 of the operation unit 101. In this case, the respective tilt angles, that is, $\theta_{71}$, $\theta_{72}$, $\theta_{70}$, $\theta_{73}$, and $\theta_{74}$, are, for example, $-25°$, $-20°$, $0°$, $+20°$, and $+25°$, respectively. Resistances R1, R2, R0, R3, and R4 respectively correspond to $\theta_{71}$, $\theta_{72}$, $\theta_{70}$, $\theta_{73}$, and $\theta_{74}$.

When the joystick 1 exists in the region of tilt angles of $-20°$ to $+20°$ respectively corresponding to the resistances R2, R0, and R3, the above arrangement holds the tilt angle of the joystick 1. At this time, the control unit 51 controls the driving position of the X-axis driving motor 103 based on an output from the second detection unit 7 which changes with a change in the tilt angle of the joystick 1. This makes it possible to perform fine alignment.

When the joystick 1 exists in the region of tilt angles of $-25°$ to $-20°$ respectively correspond to the resistances R1 to R2 and in the region of tilt angles of $+20°$ to $+25°$ respectively correspond to the resistances R3 to R4, the above mechanism restores the tilt angle of the joystick 1 to the predetermined angle $\theta_{72}$ or $\theta_{73}$. At this time, the control unit 51 controls the driving velocity of the X-axis driving motor 103 based on an output from the second detection unit 7 which changes with a change in the tilt angle of the joystick 1. That is, it is possible to greatly move the inspection unit 110.

Figure 8:
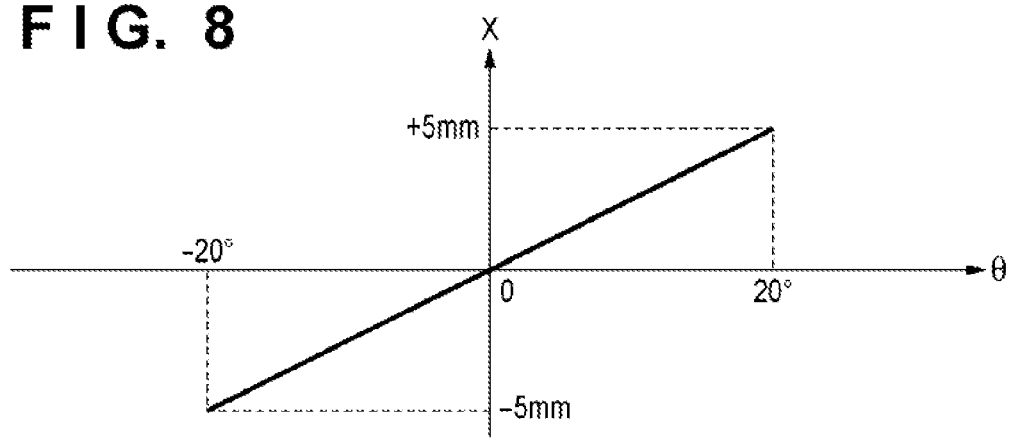
FIG. 8 is a view for explaining control in a fine operation region.

FIG. 8 shows a moving amount X of the operation unit 101 in a direction LR which corresponds to the tilt angle $\theta$ of the joystick 1 in the LR direction. A tilt angle $\theta_0$ of the joystick 1 when it stands upright is set to $0°$.

When the examiner maintains the tilt angle $\theta$ of the joystick 1 in the range of $-20°$ to $+20°$, the control unit 51 controls the X-axis driving motor 103 so as to drive the inspection unit 110 within the range of $-5$ mm to $+5$ mm in proportion to the tilt angle $\theta$ from a tilt angle of $0°$.

Figure 9:
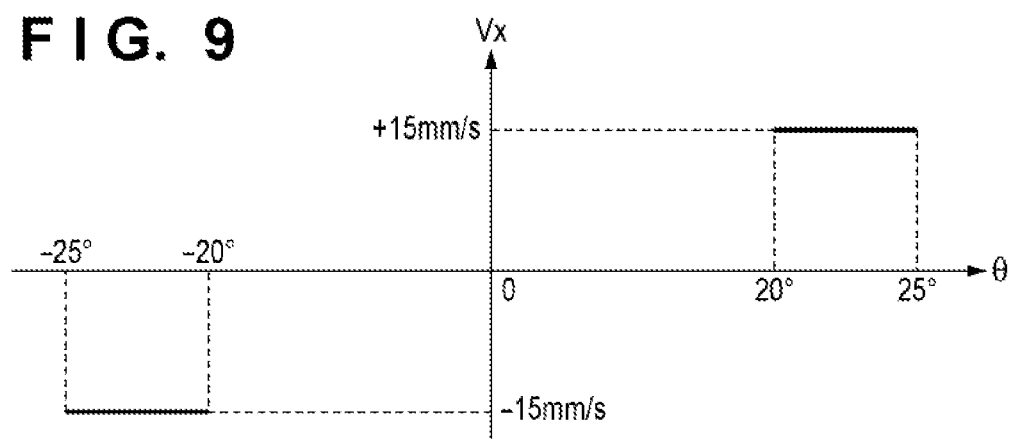
FIG. 9 is a view for explaining control in a coarse operation region.

FIG. 9 shows a moving velocity Vx of the operation unit 101 in the LR direction which corresponds to the tilt angle θ of the joystick 1 in the LR direction. When the examiner holds the tilt angle θ within the range of more than −20° and less than −25°, the control unit 51 controls the X-axis driving motor 103 so as to drive the inspection unit 110 at a velocity of 15 mm/s in the tilting direction of the joystick 1. Likewise, when the examiner holds the tilt angle θ within the range of more than +20° and less than +25°, the control unit 51 controls the X-axis driving motor 103 so as to drive the inspection unit 110 at a velocity of 15 mm/s in the tilting direction of the joystick 1.

A method of controlling the control unit 51 when the joystick 1 tilts in the LR (leftward/rightward) direction has been described above. The same control can be applied to a case in which the joystick 1 tilts in the FB (forward/backward) direction, and hence a detailed description of it will be omitted.

Figure 10:
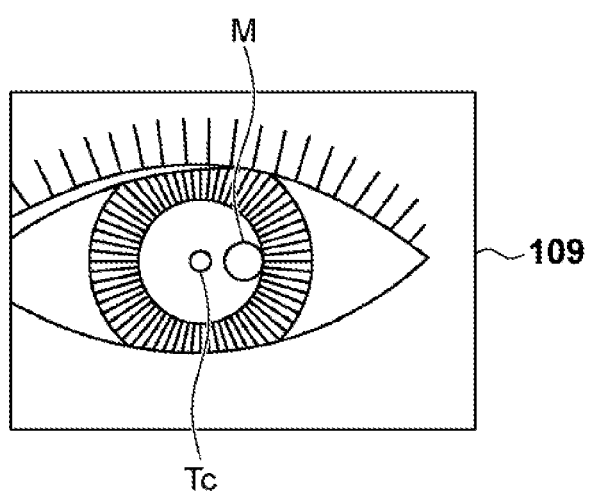
FIG. 10 is a view for explaining a state in which the center of an eye to be examined is located near an alignment mark on a monitor.

FIG. 10 is a view for explaining an anterior eye part image of the eye E on the LCD monitor 109. The LCD monitor 109 is displaying a state in which an eye center Tc is only slightly spaced apart from an alignment mark M. When aligning the inspection unit 110 in the leftward/rightward direction, the examiner operates the joystick 1 to place the eye center Tc in the alignment mark M while monitoring the LCD monitor 109. In this case, since the eye center Tc is only slightly spaced apart from the alignment mark M, the examiner tries to perform precision alignment. Therefore, an arrangement configured to move the eye center Tc in proportion to the tilt angle θ of the joystick 1 improves the operability for the operator because when the examiner excessively moves the eye center Tc, he/she is only required to return the tilt angle θ of the joystick 1 by an angle corresponding to the distance he/she has excessively moved the eye center Tc.

FIG. 11 is a view for explaining an anterior eye part image of the eye E on the LCD monitor 109. Note that this view shows a case in which the eye center Tc is greatly spaced apart from the alignment mark M, unlike the case in FIG. 10. In this case, the examiner wants to move the eye center Tc near to the alignment mark M quickly, he/she keeps tilting the joystick 1 against restoring force so as to set θ to 20° or more. With this operation, the inspection unit 110 moves in the tilting direction of the joystick 1 at a constant velocity of 15 mm/s, thereby allowing quick alignment. After the eye center Tc has approached the alignment mark M as shown in FIG. 10, the examiner decreases the force applied to the joystick 1. With this operation, owing to the restoring force described above, the joystick 1 returns to the position where the tilt angle θ becomes 20°. If the tilt angle becomes a predetermined tilt angle or less (20° or less), the velocity control is switched to position control (distance control) to allow precision alignment afterward.

Alignment of the inspection unit 110 in the forward/backward (FB) direction is performed in the same manner as alignment of the inspection unit 110 in the leftward/rightward (LR) direction. That is, when performing accurate focus adjustment while the inspection unit 110 has already been located near the best focus position, the examiner tilts the joystick 1 to the range of −20° to +20° in which a frictional force acts to perform position control. If the focus is greatly shifted from the best focus position, the examiner tilts the joystick 1 against the restoring force described above to 20° or more to perform velocity control.

In this case, even if the alignment in the leftward/rightward (LR) direction and forward/backward (FB) direction is not correct, tilting the joystick 1 in an oblique direction can simultaneously perform alignment in both the directions. At this time, according to this embodiment, it is possible to perform quick and fine alignment because it is possible to implement the operation unit 101 with a constant operating force regardless of the operating direction.

FIG. 12 is a graph showing the resistance of the first detection unit 6 (or the second detection unit 7) which corresponds to the tilt angle of the joystick 1. Unlike the graph 7002, this graph adds a resistance R2a corresponding to a tilt angle of −21° and a resistance R3a corresponding to a tilt angle of +21°. When the examiner tilts the joystick 1 from the fine operation region (the range of −20° to +20°) to the coarse region (the range of −20° to −25°), the control unit 51 does not drive the driving unit 116 if an output from the first detection unit 6 (or the second detection unit 7) which corresponds to a tilt angle between −20° to −21° falls between R2 and R2a. Likewise, when the examiner tilts the joystick 1 from the fine operation region (the range of −20° to +20°) to the coarse region (the range of −20° to +25°), the control unit 51 does not drive the driving unit 116 if an output from the first detection unit 6 (or the second detection unit 7) which corresponds to a tilt angle between +20° to +21° falls between R3 and R3a. This can prevent the inspection unit 110 from performing coarse operation when the examiner has an intention to perform fine operation. This can therefore provide the examiner with comfortable operability and allows to perform safe aligning operation for an object.

Like FIG. 12, FIG. 13 is a graph showing the resistance of the first detection unit 6 (or the second detection unit 7) which corresponds to the tilt angle of the joystick 1. Unlike FIG. 12, however, FIG. 13 adds, as set values, a resistance R2b corresponding to a tilt angle of −20.5° and a resistance R3b corresponding to a tilt angle of +20.5°. When the examiner operates the joystick 1 in a direction to exceed −20° from the fine operation region (the range of −20° to +20°) to the coarse operation region, the control unit 51 does not drive the driving unit 116 if an output from the first detection unit 6 (or the second detection unit 7) falls between R2 and R2a, as in the above case. The control unit 51 then starts velocity control from the output R2a from the first detection unit 6 (or the second detection unit 7) which corresponds to −21°. When the examiner operates the joystick 1 in a direction to return from the coarse operation region to the fine operation region, the control unit 51 ends the velocity control at the output R2b from the first detection unit 6 (or the second detection unit 7) which corresponds to −20.5°. Setting different thresholds for the start of velocity control and the end of velocity control in this manner can prevent the unstable operation of the driving unit 116 which occurs when the joystick 1 is held at an intermediate position between the start of velocity control and the end of velocity control. This can provide the object with a sense of safety.

The above description is about the case in which when the examiner operates the joystick 1 from the fine operation region to the coarse operation region, the control unit 51 sends a control signal to the driving unit 116 to drive at a constant velocity.

Figure 14:
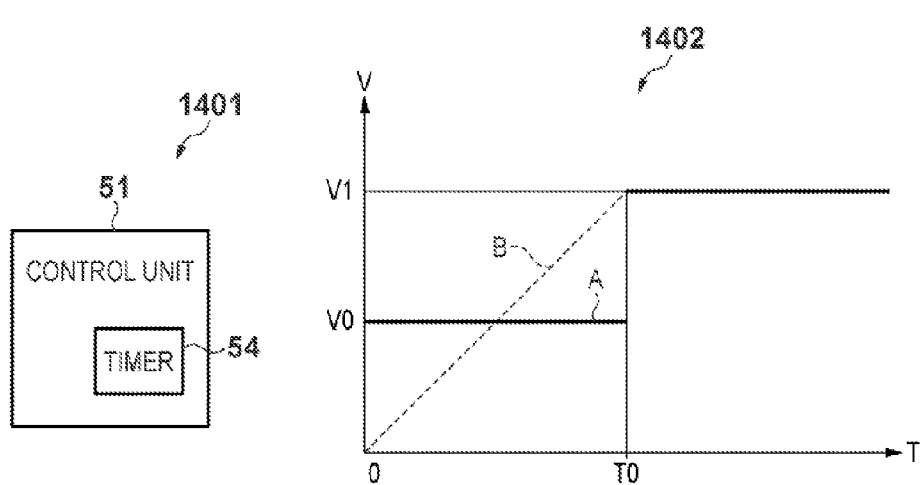
FIG. 14 is a view for explaining control of a coarse operation velocity based on a driving time.

A further modification will be described with reference to FIG. 14. Reference numeral 1401 denotes the control unit 51 including a timer 54; and 1402, the relationship between an elapsed time T and a velocity V of the driving unit 116 when the origin is set to the instant when the examiner operates the joystick 1 from the fine operation region to the coarse operation region. A line A indicates a case in which the control unit 51 controls the driving unit 116 to move at a velocity $V_0$ until the elapse of $T_0$ sec (predetermined time), and controls the driving unit 116 to move at $V_1$ higher than $V_0$ after the elapse of $T_0$. In this case, the inspection unit 110 abruptly increases its velocity at the instant when the operation unit 101 shifts from the fine operation region to the coarse operation region.

In contrast, a line B indicates a case in which the control unit 51 sends driving signals to the driving unit 116 to gradually increase its velocity until the elapse of $T_0$ sec and set the velocity $V_1$ after the elapse of $T_0$ sec. This can prevent a phenomenon that the inspection unit 110 abruptly increases its velocity at the instant when the operation unit 101 shifts from the fine operation region to the coarse operation region. This can give the examiner a sense of safety. In this case, the line B indicates that the driving velocity V of the driving unit 116 increases in proportion to the time T after the operation unit 101 shifts from the fine operation region to the coarse operation region. Even if, however, the line B is nonlinear, a similar effect can be obtained.

Figure 15:
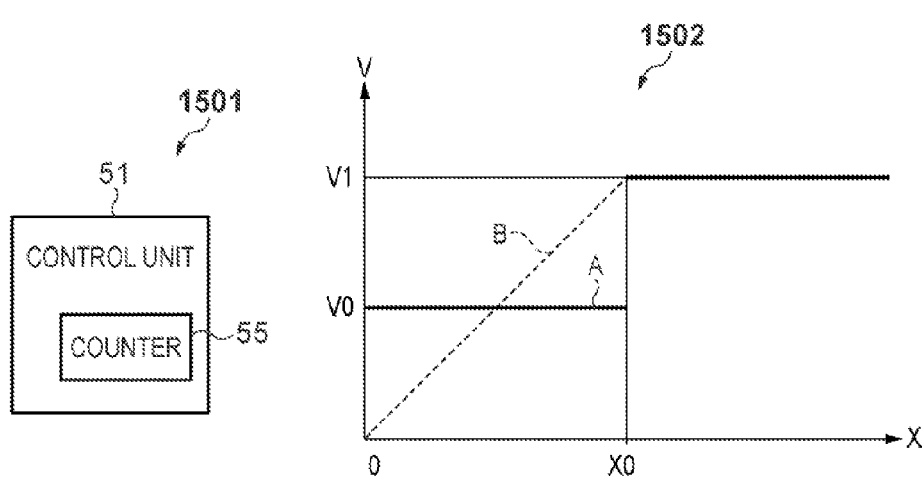
FIG. 15 is a view for explaining control of a coarse operation velocity based on a driving distance.

Still another modification will be described with reference to FIG. 15. Reference numeral 1501 denotes the control unit 51 including a counter 55 which stores the driving amount of the driving unit 116; and 1502, the relationship between the velocity V of the driving unit 116 and the driving amount X (change amount X) by which the driving unit 116 is driven after the examiner operates the joystick 1 from the fine operation region to the coarse operation region. Referring to FIG. 14, the control unit 51 changes the velocity V of the driving unit 116 in accordance with the time T after the examiner operates the joystick 1 from the fine operation region to the coarse operation region. As indicated by reference numeral 1502, it is possible to change the velocity V of the driving unit 116 in accordance with the amount by the driving unit 116 driven after the examiner operates the joystick 1 from the fine operation region to the coarse operation region.

As described with reference to the graph 1402, referring to the graph 1502, a line A indicates a case in which the control unit 51 controls the driving unit 116 to move at the velocity $V_0$ until the driving amount reaches $X_0$, and then controls the driving unit 116 to move at $V_1$ higher than $V_0$ after the driving amount reaches $X_0$. In this case as well, the inspection unit 110 abruptly increases its velocity at the instant when the operation unit 101 shifts from the fine operation region to the coarse operation region. In contrast, a line B indicates a case in which the control unit 51 sends driving signals to the driving unit 116 to gradually increase the velocity until the driving amount reaches $X_0$ and then set it to the velocity $V_1$ after the driving amount reaches $X_0$. This can prevent the phenomenon that the inspection unit 110 abruptly increases its velocity at the instant when the operation unit 101 shifts from the fine operation region to the coarse operation region. This can give the examiner a sense of safety. In this case, a line B indicates that the driving velocity V of the driving unit 116 increases in proportion to the driving amount X after the operation unit 101 shifts from the fine operation region to the coarse operation region. Even if, however, the line B is nonlinear, a similar effect can be obtained.

Figure 16:
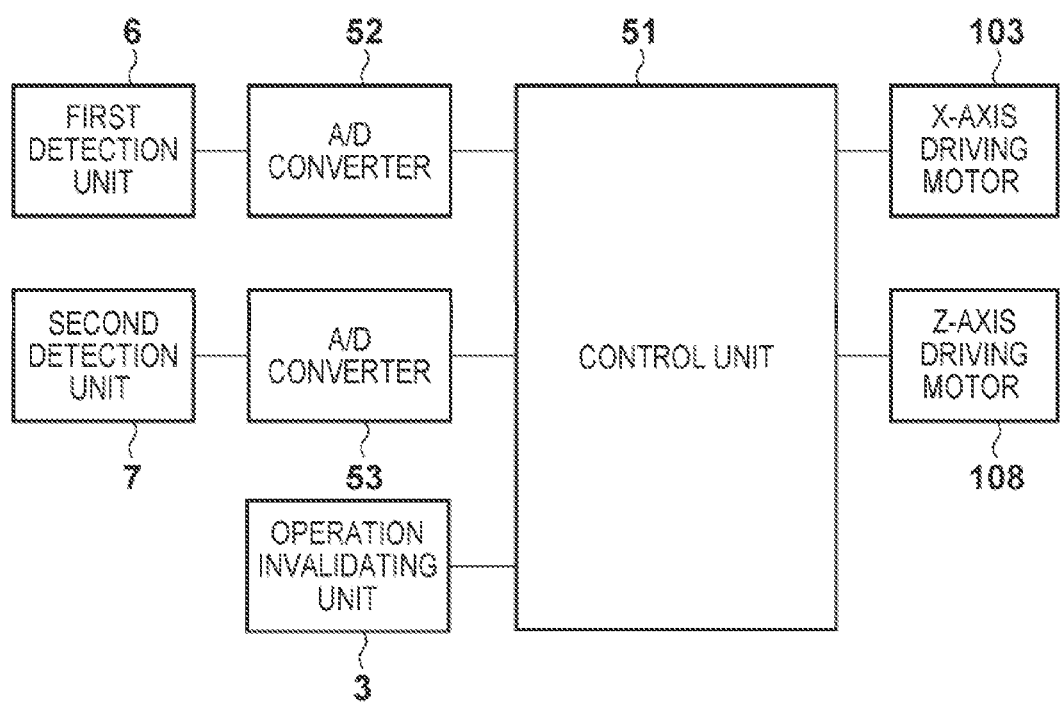
FIG. 16 is a functional block diagram including an operation invalidating unit.

Note that this embodiment has exemplified the arrangement in which when the examiner tilts the joystick 1, the control unit 51 sends some driving signals to the driving unit 116. However, the present invention is not limited to this arrangement, and may have another arrangement, which will be described with reference to the functional block diagram of FIG. 16. In this arrangement, the operation invalidating unit 3 is connected to the control unit 51, in addition to the components of the functional arrangement described with reference to FIG. 6. The control unit 51 transmits driving signals to the X-axis driving motor 103 and the Z-axis driving motor 108 based on signals input from the first detection unit 6 and the second detection unit 7 via the A/D converters 52 and 53 and the signal from the operation invalidating unit 3. In this case, the operation invalidating unit 3 is a momentary type button. The control unit 51 transmits an invalidation signal for inhibiting driving operation only while the examiner presses the operation invalidating unit 3.

Therefore, when aligning operation is almost complete while the joystick 1 is in the tilted state as shown in FIG. 10, restoring the joystick 1 to the neutral state while operating the operation invalidating unit 3 can achieve an improvement in the operability of fine alignment by fine operation.

In addition, in this embodiment, when the joystick 1 is tiled in the FB (forward/backward) direction, fine operation and velocity control are performed as in the case in which the joystick 1 is tilted in the LR (leftward/rightward) direction. However, the present invention is not limited to this. That is, when the joystick 1 is tilted in the F (forward) direction up to the coarse operation region, the control unit 51 may inhibit the transmission of a driving signal to the Z-axis driving motor 108. This can prevent coarse operation from being started due to an operation error by the examiner when performing aligning operation, thereby preventing contact between the eye E and the inspection unit. In addition, since there is no possibility that the inspection unit moves at high speed toward the eye E from a position near the eye E, it is possible to reduce the sense of fear felt by the object.

(Second Embodiment)

Sectional views of an operation unit 101 according to the second embodiment will be described with reference to FIG. 17. Only a modification of the arrangement for generating operating force will be described below, and a description of other arrangements, for example, the overall arrangement of the operation unit 101 and an arrangement and control for detecting a tilt angle will be omitted.

Reference numeral 1701 denotes the neutral state of a joystick 1. A bearing base 202 is placed below a joystick shaft 201 joined to the joystick 1. A central ball 203 is attached to the joystick shaft 201 on the lower side of the opening portion of the bearing base 202. A compression spring 204 (to be described later) biases the central ball 203 against the opening portion of the bearing base 202. This allows the joystick 1 to perform tilting operation using the curvature center of the central ball 203 as the tilt center. A moving unit 205 is placed below the joystick shaft 201. A hollow portion is formed on the upper end side of the moving unit 205, in which the joystick shaft 201 is fitted. The moving unit 205 can slide in the axial direction of the joystick shaft 201. The moving unit 205 has an approximate spherical shape. An operating force generation unit 206 joined to the bearing base 202 is provided below the moving unit 205. An approximate spherical surface 206a centered on the curvature center of the central ball 203 is formed on the operating force generation unit 206. A restoration portion 206b having an inclined surface is formed on the outer circumferential portion of the approximate spherical surface 206a. The compression spring 204 as an elastic member is provided between the joystick shaft 201 and the moving unit 205. The compression spring 204 biases the central ball 203 against the bearing base 202, and also biases the moving unit 205 against the operating force generation unit 206.

Reference numeral 1702 denotes a state in which the joystick 1 tilts by a predetermined angle $\theta_1$; and 1703, a state in which the joystick 1 tilts by a predetermined angle $\theta_2$. The predetermined angle $\theta_1$ indicates the maximum tilt angle of a tilt holding region, and $\theta_2$ indicates the maximum tilt angle of a tilt restoration region.

First of all, when the joystick 1 is tilted in the tilt holding region (a tilt angle between $\theta_0$ and $\theta_1$) (see reference numeral 1701), the compression spring 204 biases the moving unit 205 against the approximate spherical surface 206a of the operating force generation unit 206. At this time, a frictional force is generated between the moving unit 205 and the operating force generation unit 206. With this frictional force, it is possible to hold the tilt angle of the joystick 1. In addition, since the approximate spherical surface 206a of the operating force generation unit 206 is formed with a curvature centered on the tilt center, even if the examiner moves the joystick 1 in an arbitrary direction in the tilt holding region, the compression spring 204 does not expand or contract. This makes it possible to generate constant frictional force regardless of the operating direction of the joystick 1. This makes it possible to hold the operating force constant in an arbitrary direction.

When the joystick 1 is tilted to the tilt restoration region (a tilt angle equal to or more than $\theta_1$) (see reference numeral 1702), the approximate spherical surface of the moving unit 205 comes into contact with the restoration portion 206b having an inclined surface shape formed on the operating force generation unit 206. When the examiner further tilts the joystick 1 (see reference numeral 1703), the moving unit 205 moves in the axial direction with a component of the force received from the inclined surface in the axial direction of the joystick shaft 201. At this time, the compression spring 204 is compressed. In this case, when the examiner stops holding the joystick 1, the stretching force of the compression spring 204 generates a force in the moving unit 205 to restore toward the center. With this restoring force, the joystick shaft 201, that is, the joystick 1, restores to the predetermined angle $\theta_1$ indicated by 1702.

This embodiment can provide an ophthalmologic apparatus including a joystick mechanism which can obtain a uniform operational feeling with a simple arrangement.

(Third Embodiment)

Sectional views of an operation unit 101 according to the third embodiment will be described with reference to FIG. 18. Only a modification of the arrangement for generating an operating force will be described below, and a description of other arrangements, for example, the overall arrangement of the operation unit 101 and an arrangement and control for detecting a tilt angle will be omitted.

Reference numeral 1801 denotes the neutral state of a joystick 1. Bearings 302a and 302b are arranged below a joystick shaft 301 joined to the joystick 1. A central ball 303 is attached to the joystick shaft 301 on the lower side of the opening portions of the bearings 302a and 302b. This allows the joystick 1 to perform tilting operation using the curvature center of the central ball 303 as the tilt center. An approximate spherical portion 301a is formed on the lower end of the joystick shaft 301. A moving portion 305 as a member having a disk-like shape having, in its center, a hole fitted on the approximate spherical portion 301a is placed. The moving portion 305 is sandwiched between a frictional member 306 and an operating force generation unit 307.

A flat surface portion 307a and an inclined surface portion 307b are formed on the operating force generation unit 307. The outer circumferential portion of the operating force generation unit 307 is fitted on the frictional member 306. The operating force generation unit 307 can move in the upward/downward direction as shown in FIG. 18. A compression spring 308 is placed below the operating force generation unit 307. The other end of the compression spring 308 is pressed against a base 309.

Reference numeral 1802 denotes a state in which the joystick 1 tilts by a predetermined angle $\theta_1$; and 1803, a state in which the joystick 1 tilts by a predetermined angle $\theta_2$. The predetermined angle $\theta_1$ indicates the maximum tilt angle of a tilt holding region, and $\theta_2$ indicates the maximum tilt angle of a tilt restoration region.

First of all, when the joystick 1 is tilted in the tilt holding region (a tilt angle between $\theta_0$ and $\theta_1$) (see reference numeral 1801), the compression spring 308 biases the moving portion 305 against the flat surface portion 307a of the operating force generation unit 307. At this time, a frictional force is generated between the moving portion 305, the operating force generation unit 307, and the frictional member 306. With this frictional force, it is possible to hold the tilt angle of the joystick 1. In addition, the approximate spherical portion 301a formed on the lower end of the joystick shaft 301 makes the moving portion 305 move synchronously with the movement of the joystick shaft 301. The moving portion 305 moves in a horizontal plane as the joystick shaft 301 tilts. For this reason, even if the moving portion 305 is moved in an arbitrary direction in the tilt holding region, the compression spring 308 does not expand or contract. This makes it possible to generate constant frictional force regardless of the operating direction of the joystick 1. This makes it possible to hold the operating force constant in an arbitrary direction.

At this time, the compression spring 308 is compressed. In this case, when the examiner stops holding the joystick 1, the biasing force of the compression spring 308, which makes the spring expand, generates force in the moving unit 305 to restore toward the center. With this restoring force, the joystick shaft 301, that is, the joystick 1, restores to the predetermined angle $\theta_1$ indicated by reference numeral 1802.

This embodiment can provide an ophthalmologic apparatus including a joystick mechanism which can obtain a uniform operational feeling with a simple arrangement.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-042656 filed on Feb. 28, 2011, which is hereby incorporated by reference herein in its entirety.

What is claimed is:

1. An ophthalmologic apparatus comprising:
an inspection unit adapted to inspect an eye to be examined;
an operation member;
a first member including a recess portion and a projection portion provided on part of the recess portion;
a second member which is integrally provided with said operation member and is configured to move in correspondence with tilting of said operation member while contacting said first member; and
a driving unit adapted to move said inspection unit based on tilting of said operation member and to coarsely move said inspection unit in a case where said second member is in contact with the projection portion, wherein in a case where said second member is in contact with the projection portion, a distance between a tilt center of said operation member and said second member is shorter than a distance between the tilt center of said operation member and said second member in a case where said second member is not in contact with the projection portion.

2. The apparatus according to claim 1, further comprising an elastic member provided between the tilt center of said operation member and said second member,
wherein in a case where said second member is in contact with the projection portion, said elastic member provides a force directed towards returning the distance between the tilt center of the operation member and the second member to its original distance when the second member is not in contact with the projection portion.

3. The apparatus according to claim 2, wherein before said second member comes into contact with the projection portion, said elastic member acts to hold a position of said second member relative to said first member.

4. The apparatus according to claim 1, further comprising:
a detection unit adapted to detect a tilt angle from a non-tilt position of said operation member; and
a generation unit adapted to generate a predetermined frictional force for holding tilt of said operation member in a first case in which the tilt angle is not more than a predetermined tilt angle and generate a restoring force for restoring tilt of said operation member to the predetermined tilt angle in a second case in which the tilt angle exceeds the predetermined tilt angle.

5. The apparatus according to claim 4, wherein a central member provided at the tilt center of said operation member has a spherical shape.

6. The apparatus according to claim 4, further comprising a biasing unit adapted to bias said second member,
wherein said generation unit comprises a restoration member provided to compress said biasing unit, and generates the restoring force in accordance with a biasing force generated by said biasing unit compressed by said restoration member.

7. The apparatus according to claim 4, wherein said driving unit moves said inspection unit to a position corresponding to the tilt of said operation member in the first case, and
wherein said driving unit moves said inspection unit at a velocity corresponding to the tilt of said operation member in the second case.

8. The apparatus according to claim 4, wherein (a) a predetermined tilt angle when control ends in the first case and a predetermined tilt angle when control starts in the second case have different values, or (b) a predetermined tilt angle when control starts in the second case and a predetermined tilt angle when control ends in the second case have different values.

9. The apparatus according to claim 7, wherein said driving unit changes the velocity in accordance with an elapsed time from a start of control in the second case.

10. The apparatus according to claim 9, wherein said driving unit increases the velocity in proportion to an elapsed time from a start of control in the second case, and makes the velocity constant after a predetermined time has elapsed since a start of control in the second case.

11. The apparatus according to claim 7, wherein said driving unit changes the velocity in accordance with a change amount of the position from a start of control in the second case.

12. The apparatus according to claim 11, wherein said driving unit increases the velocity in proportion to a change amount of the position from a start of control in the second case, and makes the velocity constant after a driving amount of the position becomes a predetermined change amount.

13. The apparatus according to claim 4, further comprising a motion direction conversion unit adapted to convert tilting motion of said operation member to linear motion,
wherein said detection unit detects the tilt angle of said operation member based on a resistance of a direct-acting potentiometer in accordance with the linear motion.

14. The apparatus according to claim 4, further comprising an inhibition unit adapted to inhibit driving by said driving unit in accordance with a tilt of said operation member,
wherein said inhibition unit inhibits the driving when said inspection unit is driven in a direction to approach the eye by control in the second case in which a position of said inspection unit is changed at a velocity corresponding to tilting of said operation member.

15. The apparatus according to claim 1, wherein the driving unit is adapted to finely move said inspection unit at a speed slower than the coarse movement in a case where said second member is not in contact with the projection portion.

16. An ophthalmologic apparatus comprising:
an inspection unit adapted to inspect an eye to be examined;
an operation member;
a first member including a recess portion and a projection portion provided on part of the recess portion;
a second member which is integrally provided with said operation member and is configured to move in correspondence with tilting of said operation member while contacting said first member;
a driving unit adapted to move said inspection unit based on tilting of said operation member and to coarsely move said inspection unit in a case where said second member is in contact with the projection portion;
a detection unit adapted to detect a tilt angle from a non-tilt position of said operation member; and
a generation unit adapted to generate a predetermined frictional force for holding tilt of said operation member in a first case in which the tilt angle is not more than a predetermined tilt angle and generate a restoring force for restoring tilt of said operation member to the predetermined tilt angle in a second case in which the tilt angle exceeds the predetermined tilt angle.

* * * * *